(12) United States Patent
Hong et al.

(10) Patent No.: US 11,702,640 B2
(45) Date of Patent: Jul. 18, 2023

(54) MONOOXYGENASE MUTANT, PREPARATION METHOD AND APPLICATION THEREOF

(71) Applicant: ASYMCHEM LABORATORIES (TIANJIN) CO., LTD., TEDA Tianjin (CN)

(72) Inventors: Hao Hong, Morrisville, NC (US); James Gage, Morrisville, NC (US); Jiangping Lu, Tianjin (CN); Xuecheng Jiao, Tianjin (CN); Na Zhang, Tianjin (CN); Rui Li, Tianjin (CN); Kejian Zhang, Tianjin (CN); Yu Zhang, Tianjin (CN)

(73) Assignee: ASYMCHEM LABORATORIES (TIANJIN) CO., LTD., Tianjin (CN)

( * ) Notice: Subject to any disclaimer, the term of this patent is extended or adjusted under 35 U.S.C. 154(b) by 0 days.

(21) Appl. No.: 16/966,548

(22) PCT Filed: Feb. 8, 2018

(86) PCT No.: PCT/CN2018/075811
§ 371 (c)(1),
(2) Date: Jul. 31, 2020

(87) PCT Pub. No.: WO2019/153183
PCT Pub. Date: Aug. 15, 2019

(65) Prior Publication Data
US 2020/0362318 A1   Nov. 19, 2020

(30) Foreign Application Priority Data
Feb. 7, 2018  (CN) .......................... 201810123656.0

(51) Int. Cl.
*C12N 9/02* (2006.01)
*C12N 15/53* (2006.01)

(52) U.S. Cl.
CPC .... *C12N 9/0073* (2013.01); *C12Y 114/13022* (2013.01)

(58) Field of Classification Search
None
See application file for complete search history.

(56) References Cited

U.S. PATENT DOCUMENTS

| 7,105,296 B2 | 9/2006 | Bramucci |
| 2004/0267001 A1 | 12/2004 | Bramucci |

FOREIGN PATENT DOCUMENTS

| CN | 105695425 A | 6/2016 |
| CN | 107384880 A | 11/2017 |
| WO | 03020890 A2 | 3/2003 |
| WO | 2013179005 A1 | 12/2013 |

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
UniProt Database Accession No. A0A369AK95, Apr. 2021, 1 page (Year: 2021).*
International Search Report for corresponding application PCT/CN2018/075811 filed Feb. 8, 2018; dated Nov. 15, 2018.
Bramucci M G., "Baeyer-Villiger Monooxygenase protein CHX", Dec. 18, 2003, XP055834069.
European Search Report for corresponding application EP 18 90 5606; dated Sep. 3, 2021.
Margaret Kayser, "Designer reagebts recombinant microorganisms: new and powerful tool for organic synthesis", Tetrahedon 65 (2009) 947-974.
Ronald Eastham Graham, "GenBank AAR99068", Dec. 5, 2013, XP055833787.

* cited by examiner

Primary Examiner — David Steadman
(74) Attorney, Agent, or Firm — Cantor Colburn LLP

(57) ABSTRACT

The present application relates to the technical field of genetic engineering, and provides a monooxygenase mutant, a preparation method and application thereof. The monooxygenase mutant has any one of the amino acid sequences shown in (I) and (II): (I) an amino acid sequence having at least 80% identity with the amino acid sequence shown in SEQ ID NO. 1; and (II) an amino acid sequence obtained by modifying, substituting, deleting, or adding one or several amino acids to the amino acids at 23 to 508 positions of the amino acid sequence shown in SEQ ID NO. 1, the substituting referring to a substitution of 1 to 34 amino acids, wherein the mutant has the activity of monooxygenase.

9 Claims, No Drawings
Specification includes a Sequence Listing.

SEQUENCE LISTING

<160> NUMBER OF SEQ ID NOS: 88

<210> SEQ ID NO 1
<211> LENGTH: 537
<212> TYPE: PRT
<213> ORGANISM: Brachymonas petroleovorans

<400> SEQUENCE: 1

```
Met Ser Ser Ser Pro Ser Ser Ala Ile His Phe Asp Ala Ile Val Val
1               5                   10                  15

Gly Ala Gly Phe Gly Gly Met Tyr Met Leu His Lys Leu Arg Asp Gln
            20                  25                  30

Leu Gly Leu Lys Val Lys Val Phe Asp Thr Ala Gly Gly Ile Gly Gly
        35                  40                  45

Thr Trp Tyr Trp Asn Arg Tyr Pro Gly Ala Leu Ser Asp Thr His Ser
    50                  55                  60

His Val Tyr Gln Tyr Ser Phe Asp Glu Ala Met Leu Gln Glu Trp Thr
65                  70                  75                  80

Trp Lys Asn Lys Tyr Leu Thr Gln Pro Glu Ile Leu Ala Tyr Leu Glu
                85                  90                  95

Tyr Val Ala Asp Arg Leu Asp Leu Arg Pro Asp Ile Gln Leu Asn Thr
            100                 105                 110
```

```
Thr Val Thr Ser Met His Phe Asn Glu Val His Asn Ile Trp Glu Val
        115                 120                 125

Arg Thr Asp Arg Gly Gly Tyr Tyr Thr Ala Arg Phe Ile Val Thr Ala
    130                 135                 140

Leu Gly Leu Leu Ser Ala Ile Asn Trp Pro Asn Ile Pro Gly Arg Glu
145                 150                 155                 160

Ser Phe Gln Gly Glu Met Tyr His Thr Ala Ala Trp Pro Lys Asp Val
                165                 170                 175

Glu Leu Arg Gly Lys Arg Val Gly Val Ile Gly Thr Gly Ser Thr Gly
            180                 185                 190

Val Gln Leu Ile Thr Ala Ile Ala Pro Glu Val Lys His Leu Thr Val
        195                 200                 205

Phe Gln Arg Thr Pro Gln Tyr Ser Val Pro Thr Gly Asn Arg Pro Val
    210                 215                 220

Ser Ala Gln Glu Ile Ala Glu Val Lys Arg Asn Phe Ser Lys Val Trp
225                 230                 235                 240

Gln Gln Val Arg Glu Ser Ala Val Ala Phe Gly Phe Glu Glu Ser Thr
                245                 250                 255

Val Pro Ala Met Ser Val Ser Glu Ala Glu Arg Gln Arg Val Phe Gln
            260                 265                 270

Glu Ala Trp Asn Gln Gly Asn Gly Phe Tyr Tyr Met Phe Gly Thr Phe
        275                 280                 285

Cys Asp Ile Ala Thr Asp Pro Gln Ala Asn Glu Ala Ala Ala Thr Phe
    290                 295                 300

Ile Arg Asn Lys Ile Ala Glu Ile Val Lys Asp Pro Glu Thr Ala Arg
305                 310                 315                 320

Lys Leu Thr Pro Thr Asp Val Tyr Ala Arg Arg Pro Leu Cys Asp Ser
                325                 330                 335

Gly Tyr Tyr Arg Thr Tyr Asn Arg Ser Asn Val Ser Leu Val Asp Val
            340                 345                 350

Lys Ala Thr Pro Ile Ser Ala Met Thr Pro Arg Gly Ile Arg Thr Ala
        355                 360                 365

Asp Gly Val Glu His Glu Leu Asp Met Leu Ile Leu Ala Thr Gly Tyr
    370                 375                 380

Asp Ala Val Asp Gly Asn Tyr Arg Arg Ile Asp Leu Arg Gly Arg Gly
385                 390                 395                 400

Gly Gln Thr Ile Asn Glu His Trp Asn Asp Thr Pro Thr Ser Tyr Val
                405                 410                 415

Gly Val Ser Thr Ala Asn Phe Pro Asn Met Phe Met Ile Leu Gly Pro
            420                 425                 430

Asn Gly Pro Phe Thr Asn Leu Pro Pro Ser Ile Glu Ala Gln Val Glu
        435                 440                 445

Trp Ile Thr Asp Leu Val Ala His Met Arg Gln His Gly Leu Ala Thr
    450                 455                 460

Ala Glu Pro Thr Arg Asp Ala Glu Asp Ala Trp Gly Arg Thr Cys Ala
465                 470                 475                 480

Glu Ile Ala Glu Gln Thr Leu Phe Gly Gln Val Glu Ser Trp Ile Phe
                485                 490                 495

Gly Ala Asn Ser Pro Gly Lys Lys His Thr Leu Met Phe Tyr Leu Ala
            500                 505                 510

Gly Leu Gly Asn Tyr Arg Lys Gln Leu Ala Asp Val Ala Asn Ala Gln
        515                 520                 525
```

```
Tyr Gln Gly Phe Ala Phe Gln Pro Leu
    530                 535
```

<210> SEQ ID NO 2
<211> LENGTH: 1614
<212> TYPE: DNA
<213> ORGANISM: Brachymonas petroleovorans

<400> SEQUENCE: 2

| | |
|---|---|
| atgagtagca gcccgagcag cgccatccac tttgacgcca ttgtggtggg tgccggtttt | 60 |
| ggcggcatgt atatgctgca caagctgcgc gaccagctgg gcctgaaagt taaagtgttc | 120 |
| gacaccgccg gtggtattgg tggtacctgg tactggaacc gctatccggg tgccctgagc | 180 |
| gacacccata gccacgtgta ccagtacagc ttcgatgagg ccatgctgca ggagtggaca | 240 |
| tggaaaaata aatatctgac ccagccggaa atcctggcat atctggaata cgtggccgat | 300 |
| cgtctggatt tacgccctga cattcagctg aacaccaccg ttaccagcat gcattttaac | 360 |
| gaggtgcaca atatctggga agttcgcacc gatcgtggcg gctactatac agcacgcttc | 420 |
| attgtgaccg cactgggtct gttaagtgcc atcaactggc cgaacatccc gggccgtgag | 480 |
| tcttttcaag gcgaaatgta tcataccgcc gcctggccga agatgttgaa ctgcgcggc | 540 |
| aagcgcgtgg gtgtgatcgg tacaggtagc accggtgtgc agctgatcac cgccattgca | 600 |
| ccggaggtga agcacctgac cgttttcag cgtaccccgc agtatagcgt tccgacaggc | 660 |
| aatcgcccgg ttagcgccca ggaaatcgca gaagtgaaac gcaactttag caaagtgtgg | 720 |
| cagcaggtgc gtgagagtgc cgttgccttt ggctttgagg aaagcaccgt gccggcaatg | 780 |
| agcgttagcg aggcagaacg ccagcgtgtt ttccaggaag catggaatca gggcaacggc | 840 |
| ttttactata tgtttggcac cttttgcgat atcgccacag atccgcaggc caacgaggca | 900 |
| gccgccacct tcattcgtaa taagatcgcc gaaatcgtta agatccgga cagcccgc | 960 |
| aaactgacac cgacagacgt ttatgcccgt cgtccgctgt gcgatagcgg ctactatcgc | 1020 |
| acctacaatc gtagcaacgt gagcctggtg gatgtgaagg ccaccccgat cagtgcaatg | 1080 |
| accccgcgcg gcattcgtac cgcagatggc gtggagcatg aactggacat gctgattctg | 1140 |
| gcaaccggct acgacgccgt tgatggcaac tatcgccgta ttgatctgcg tggccgcggt | 1200 |
| ggccagacca ttaacgaaca ctggaatgac cccctacca gctatgttgg cgtgagcacc | 1260 |
| gccaattttc cgaacatgtt catgattctg ggccctaacg gcccgttcac caatctgccg | 1320 |
| ccgagtatcg aagcccaggt ggaatggatt accgatctgg tggcacacat gcgtcagcac | 1380 |
| ggtctggcaa ccgccgaacc tacccgcgat gccgaagatg cctggggtcg tacctgtgca | 1440 |
| gagattgccg agcagaccct gttcggccag gtggaaagct ggatctttgg cgcaaacagc | 1500 |
| ccgggtaaga agcataccct gatgttttat ctggccggcc tgggcaatta ccgcaaacag | 1560 |
| ctggccgatg tggcaaatgc ccagtatcag ggctttgcct tccagcctct gtaa | 1614 |

<210> SEQ ID NO 3
<211> LENGTH: 34
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(34)
<223> OTHER INFORMATION: Forward primer for M25A mutation

<400> SEQUENCE: 3
gccggttttg gcggcatgta tgcgctgcac aagc    34

<210> SEQ ID NO 4
<211> LENGTH: 34
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(34)
<223> OTHER INFORMATION: Reverse primer for M25A mutation

<400> SEQUENCE: 4
gcttgtgcag cgcatacatg ccgccaaaac cggc    34

<210> SEQ ID NO 5
<211> LENGTH: 33
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(33)
<223> OTHER INFORMATION: forward primer for P106R mutation
<220> FEATURE:
<221> NAME/KEY: misc_feature
<222> LOCATION: (1)..(33)
<223> OTHER INFORMATION: forward primer for P106R mutation

<400> SEQUENCE: 5
cgtctggatt tacgccgtga cattcagctg aac    33

<210> SEQ ID NO 6
<211> LENGTH: 33
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(33)
<223> OTHER INFORMATION: reverse primer for P106R mutation

<400> SEQUENCE: 6
gttcagctga atgtcacggc gtaaatccag acg    33

<210> SEQ ID NO 7
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(31)
<223> OTHER INFORMATION: forward primer for R159L mutation

<400> SEQUENCE: 7
cgaacatccc gggccttgag tcttttcaag g    31

<210> SEQ ID NO 8
<211> LENGTH: 31
<212> TYPE: DNA
<213> ORGANISM: Artificial Sequence
<220> FEATURE:

```
<223> OTHER INFORMATION: Primer designed for point mutation
<220> FEATURE:
<221> NAME/KEY: misc_feature
<222> LOCATION: (1)..(31)
<223> OTHER INFORMATION: reverse primer for R159L mutation

<400> SEQUENCE: 8
ccttgaaaag actcaaggcc cgggatgttc g                                        31

<210> SEQ ID NO 9
<211> LENGTH: 29
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(29)
<223> OTHER INFORMATION: forward primer for A265E mutation

<400> SEQUENCE: 9
gagcgttagc gaggaagaac gccagcgtg                                           29

<210> SEQ ID NO 10
<211> LENGTH: 29
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(29)
<223> OTHER INFORMATION: reverse primer for A265E mutation

<400> SEQUENCE: 10
cacgctggcg ttcttcctcg ctaacgctc                                           29

<210> SEQ ID NO 11
<211> LENGTH: 39
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(39)
<223> OTHER INFORMATION: forward primer for C289S mutation

<400> SEQUENCE: 11
tttactatat gtttggcacc tttagcgata tcgccacag                                39

<210> SEQ ID NO 12
<211> LENGTH: 39
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(39)
<223> OTHER INFORMATION: reverse primer for C289S mutation

<400> SEQUENCE: 12
ctgtggcgat atcgctaaag gtgccaaaca tatagtaaa                                39

<210> SEQ ID NO 13
<211> LENGTH: 33
<212> TYPE: DNA
<213> ORGANISM: Artificial Sequence
```

-continued

```
<220> FEATURE:
<223> OTHER INFORMATION: Primer designed for point mutation
<220> FEATURE:
<221> NAME/KEY: misc_feature
<222> LOCATION: (1)..(33)
<223> OTHER INFORMATION: forward primer for M377V mutation

<400> SEQUENCE: 13
ggagcatgaa ctggacgtgc tgattctggc aac                               33

<210> SEQ ID NO 14
<211> LENGTH: 33
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(33)
<223> OTHER INFORMATION: reverse primer for M377V mutation

<400> SEQUENCE: 14
gttgccagaa tcagcacgtc cagttcatgc tcc                               33

<210> SEQ ID NO 15
<211> LENGTH: 38
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(38)
<223> OTHER INFORMATION: forward primer for L380F mutation

<400> SEQUENCE: 15
agcatgaact ggacatgctg attttcgcaa ccggctac                          38

<210> SEQ ID NO 16
<211> LENGTH: 38
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(38)
<223> OTHER INFORMATION: reverse primer for L380F mutation

<400> SEQUENCE: 16
gtagccggtt gcgaaaatca gcatgtccag ttcatgct                          38

<210> SEQ ID NO 17
<211> LENGTH: 29
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(29)
<223> OTHER INFORMATION: forward primer for P435L mutation

<400> SEQUENCE: 17
gggccctaac ggcctgttca ccaatctgc                                    29

<210> SEQ ID NO 18
<211> LENGTH: 29
<212> TYPE: DNA
```

<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(29)
<223> OTHER INFORMATION: reverse primer for P435L mutation

<400> SEQUENCE: 18
gcagattggt gaacaggccg ttagggccc                                      29

<210> SEQ ID NO 19
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(31)
<223> OTHER INFORMATION: forward primer for F436Y mutation

<400> SEQUENCE: 19
gggccctaac ggcccgtata ccaatctgcc g                                   31

<210> SEQ ID NO 20
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(31)
<223> OTHER INFORMATION: revese primer for F436Y mutation

<400> SEQUENCE: 20
cggcagattg gtatacgggc cgttagggcc c                                   31

<210> SEQ ID NO 21
<211> LENGTH: 27
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(27)
<223> OTHER INFORMATION: forward primer for T437A mutation

<400> SEQUENCE: 21
taacggcccg ttcgccaatc tgccgcc                                        27

<210> SEQ ID NO 22
<211> LENGTH: 27
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(27)
<223> OTHER INFORMATION: reverse primer for T437A mutation

<400> SEQUENCE: 22
ggcggcagat tggcgaacgg gccgtta                                        27

<210> SEQ ID NO 23
<211> LENGTH: 34

-continued

```
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(34)
<223> OTHER INFORMATION: forward primer for L439S mutation

<400> SEQUENCE: 23
cctaacggcc cgttcaccaa ttcgccgccg agta                                34

<210> SEQ ID NO 24
<211> LENGTH: 34
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(34)
<223> OTHER INFORMATION: reverse primer for L439S mutation

<400> SEQUENCE: 24
tactcggcgg cgaattggtg aacgggccgt tagg                                34

<210> SEQ ID NO 25
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(31)
<223> OTHER INFORMATION: forward primer for A474E mutation

<400> SEQUENCE: 25
gcgatgccga agatgagtgg ggtcgtacct g                                   31

<210> SEQ ID NO 26
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(31)
<223> OTHER INFORMATION: reverse primer for A474E mutation

<400> SEQUENCE: 26
caggtacgac cccactcatc ttcggcatcg c                                   31

<210> SEQ ID NO 27
<211> LENGTH: 32
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(32)
<223> OTHER INFORMATION: forward primer for C479V mutation

<400> SEQUENCE: 27
gcctggggtc gtaccgttgc agagattgcc ga                                  32

<210> SEQ ID NO 28
```

```
<211> LENGTH: 32
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(32)
<223> OTHER INFORMATION: reverse primer for C479V mutation

<400> SEQUENCE: 28
tcggcaatct ctgcaacggt acgacccccag gc                                    32

<210> SEQ ID NO 29
<211> LENGTH: 29
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(29)
<223> OTHER INFORMATION: forward primer for Q490K mutation

<400> SEQUENCE: 29
agaccctgtt cggcaaggtg gaaagctgg                                         29

<210> SEQ ID NO 30
<211> LENGTH: 29
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(29)
<223> OTHER INFORMATION: reverse primer for Q490K mutation

<400> SEQUENCE: 30
ccagctttcc accttgccga acagggtct                                         29

<210> SEQ ID NO 31
<211> LENGTH: 34
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(34)
<223> OTHER INFORMATION: forward primer for I495A mutation

<400> SEQUENCE: 31
ccaggtggaa agctgggcct ttggcgcaaa cagc                                   34

<210> SEQ ID NO 32
<211> LENGTH: 34
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(34)
<223> OTHER INFORMATION: reverse primer for I495A mutation

<400> SEQUENCE: 32
gctgtttgcg ccaaaggccc agctttccac ctgg                                   34
```

-continued

```
<210> SEQ ID NO 33
<211> LENGTH: 33
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(33)
<223> OTHER INFORMATION: forward primer for S500I mutation

<400> SEQUENCE: 33
gctggatctt tggcgcaaac atcccgggta aga                              33

<210> SEQ ID NO 34
<211> LENGTH: 33
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(33)
<223> OTHER INFORMATION: reverse primer for S500I mutation

<400> SEQUENCE: 34
tcttacccgg gatgtttgcg ccaaagatcc agc                              33

<210> SEQ ID NO 35
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(31)
<223> OTHER INFORMATION: Forward primer for M23L mutation

<400> SEQUENCE: 35
gccggttttg gcggcttgta tatgctgcac a                                31

<210> SEQ ID NO 36
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(31)
<223> OTHER INFORMATION: Reverse primer for M23L mutation

<400> SEQUENCE: 36
tgtgcagcat atacaagccg ccaaaaccgg c                                31

<210> SEQ ID NO 37
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(31)
<223> OTHER INFORMATION: Forward primer for A74D mutation

<400> SEQUENCE: 37
acagcttcga tgaggacatg ctgcaggagt g                                31
```

```
<210> SEQ ID NO 38
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(31)
<223> OTHER INFORMATION: Reverse primer for A74D mutation

<400> SEQUENCE: 38
cactcctgca gcatgtcctc atcgaagctg t                              31

<210> SEQ ID NO 39
<211> LENGTH: 29
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(29)
<223> OTHER INFORMATION: Forward primer for M75L mutation

<400> SEQUENCE: 39
gcttcgatga ggccttgctg caggagtgg                                 29

<210> SEQ ID NO 40
<211> LENGTH: 29
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(29)
<223> OTHER INFORMATION: Reverse primer for M75L mutation

<400> SEQUENCE: 40
ccactcctgc agcaaggcct catcgaagc                                 29

<210> SEQ ID NO 41
<211> LENGTH: 35
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(35)
<223> OTHER INFORMATION: Forward primer for A93E mutation

<400> SEQUENCE: 41
ccagccggaa atcctggaat atctggaata cgtgg                          35

<210> SEQ ID NO 42
<211> LENGTH: 35
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(35)
<223> OTHER INFORMATION: Reverse primer for A93E mutation

<400> SEQUENCE: 42
ccacgtattc cagatattcc aggatttccg gctgg                          35
```

<210> SEQ ID NO 43
<211> LENGTH: 37
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(37)
<223> OTHER INFORMATION: Forward primer for L110F mutation

<400> SEQUENCE: 43
tacgccctga cattcagttc aacaccaccg ttaccag                              37

<210> SEQ ID NO 44
<211> LENGTH: 37
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(37)
<223> OTHER INFORMATION: Reverse primer for L110F mutation

<400> SEQUENCE: 44
ctggtaacgg tggtgttgaa ctgaatgtca gggcgta                              37

<210> SEQ ID NO 45
<211> LENGTH: 40
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(40)
<223> OTHER INFORMATION: Forward primer for M117A mutation

<400> SEQUENCE: 45
gaacaccacc gttaccagcg cgcattttaa cgaggtgcac                           40

<210> SEQ ID NO 46
<211> LENGTH: 40
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(40)
<223> OTHER INFORMATION: Reverse primer for M117A mutation

<400> SEQUENCE: 46
gtgcacctcg ttaaaatgcg cgctggtaac ggtggtgttc                           40

<210> SEQ ID NO 47
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(37)
<223> OTHER INFORMATION: Forward primer for T137R mutation

<400> SEQUENCE: 47
gatcgtggcg gctactatag agcacgcttc a                          31

<210> SEQ ID NO 48
<211> LENGTH: 31
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(31)
<223> OTHER INFORMATION: Reverse primer for T137R mutation

<400> SEQUENCE: 48
tgaagcgtgc tctatagtag ccgccacgat c                          31

<210> SEQ ID NO 49
<211> LENGTH: 37
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(37)
<223> OTHER INFORMATION: Forward primer for W153F mutation

<400> SEQUENCE: 49
cgggatgttc gggaagttga tggcacttaa cagaccc                    37

<210> SEQ ID NO 50
<211> LENGTH: 37
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(37)
<223> OTHER INFORMATION: Reverse primer for W153F mutation

<400> SEQUENCE: 50
gggtctgtta agtgccatca acttcccgaa catcccg                    37

<210> SEQ ID NO 51
<211> LENGTH: 35
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(35)
<223> OTHER INFORMATION: Forward primer for M166L mutation

<400> SEQUENCE: 51
tgagtctttt caaggcgaat tgtatcatac cgccg                      35

<210> SEQ ID NO 52
<211> LENGTH: 35
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(35)

<223> OTHER INFORMATION: Reverse primer for M166L mutation

<400> SEQUENCE: 52
cggcggtatg atacaattcg ccttgaaaag actca                                              35

<210> SEQ ID NO 53
<211> LENGTH: 27
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(27)
<223> OTHER INFORMATION: Forward primer for M260L mutation

<400> SEQUENCE: 53
gcaccgtgcc ggcattgagc gttagcg                                                      27

<210> SEQ ID NO 54
<211> LENGTH: 27
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(27)
<223> OTHER INFORMATION: Reverse primer for M260L mutation

<400> SEQUENCE: 54
cgctaacgct caatgccggc acggtgc                                                      27

<210> SEQ ID NO 55
<211> LENGTH: 40
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(40)
<223> OTHER INFORMATION: Forward primer for M284I mutation

<400> SEQUENCE: 55
atcagggcaa cggcttttac tatatatttg gcaccttttg                                        40

<210> SEQ ID NO 56
<211> LENGTH: 40
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(40)
<223> OTHER INFORMATION: Reverse primer for M284I mutation

<400> SEQUENCE: 56
caaaaggtgc caaatatata gtaaaagccg ttgccctgat                                        40

<210> SEQ ID NO 57
<211> LENGTH: 34
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(34)
<223> OTHER INFORMATION: Forward primer for C334L mutation

<400> SEQUENCE: 57
gcccgtcgtc cgctgttaga tagcggctac tatc                    34

<210> SEQ ID NO 58
<211> LENGTH: 34
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(34)
<223> OTHER INFORMATION: Reverse primer for C334L mutation

<400> SEQUENCE: 58
gatagtagcc gctatctaac agcggacgac gggc                    34

<210> SEQ ID NO 59
<211> LENGTH: 27
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(27)
<223> OTHER INFORMATION: Forward primer for A359E mutation

<400> SEQUENCE: 59
accccgatca gtgaaatgac cccgcgc                            27

<210> SEQ ID NO 60
<211> LENGTH: 27
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(27)
<223> OTHER INFORMATION: Reverse primer for A359E mutation

<400> SEQUENCE: 60
gcgcggggtc atttcactga tcggggt                            27

<210> SEQ ID NO 61
<211> LENGTH: 27
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(27)
<223> OTHER INFORMATION: Forward primer for M360I mutation

<400> SEQUENCE: 61
accccgatca gtgcaataac cccgcgc                            27

<210> SEQ ID NO 62
<211> LENGTH: 27
<212> TYPE: DNA
<213> ORGANISM: Artificial Sequence
<220> FEATURE:
<223> OTHER INFORMATION: Primer designed for point mutation
<220> FEATURE:

<221> NAME/KEY: misc_feature
<222> LOCATION: (1)..(27)
<223> OTHER INFORMATION: Reverse primer for M360I mutation

<400> SEQUENCE: 62
gcgcggggtt attgcactga tcggggt                                          27

<210> SEQ ID NO 63
<211> LENGTH: 35
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(35)
<223> OTHER INFORMATION: Forward primer for M426L mutation

<400> SEQUENCE: 63
ccgccaattt tccgaacttg ttcatgattc tgggc                                 35

<210> SEQ ID NO 64
<211> LENGTH: 35
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(35)
<223> OTHER INFORMATION: Reverse primer for M426L mutation

<400> SEQUENCE: 64
gcccagaatc atgaacaagt tcggaaaatt ggcgg                                 35

<210> SEQ ID NO 65
<211> LENGTH: 41
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(41)
<223> OTHER INFORMATION: Forward primer for M428F mutation

<400> SEQUENCE: 65
caattttccg aacatgttct tcattctggg ccctaacggc c                          41

<210> SEQ ID NO 66
<211> LENGTH: 41
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(41)
<223> OTHER INFORMATION: Reverse primer for M428F mutation

<400> SEQUENCE: 66
ggccgttagg gcccagaatg aagaacatgt tcggaaaatt g                          41

<210> SEQ ID NO 67
<211> LENGTH: 27
<212> TYPE: DNA
<213> ORGANISM: Artificial Sequence
<220> FEATURE:
<223> OTHER INFORMATION: Primer designed for point mutation

```
<220> FEATURE:
<221> NAME/KEY: misc_feature
<222> LOCATION: (1)..(27)
<223> OTHER INFORMATION: Forward primer for P435A mutation

<400> SEQUENCE: 67
gggccctaac ggcgcgttca ccaatct                                    27

<210> SEQ ID NO 68
<211> LENGTH: 27
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(27)
<223> OTHER INFORMATION: Reverse primer for P435A mutation

<400> SEQUENCE: 68
agattggtga acgcgccgtt agggccc                                    27

<210> SEQ ID NO 69
<211> LENGTH: 28
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(28)
<223> OTHER INFORMATION: Forward primer for F436L mutation

<400> SEQUENCE: 69
gccctaacgg cccgttaacc aatctgcc                                   28

<210> SEQ ID NO 70
<211> LENGTH: 28
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(28)
<223> OTHER INFORMATION: Reverse primer for F436L mutation

<400> SEQUENCE: 70
ggcagattgg ttaacgggcc gttagggc                                   28

<210> SEQ ID NO 71
<211> LENGTH: 30
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(30)
<223> OTHER INFORMATION: Forward primer for F436A mutation

<400> SEQUENCE: 71
gccctaacgg cccggccacc aatctgccgc                                 30

<210> SEQ ID NO 72
<211> LENGTH: 30
<212> TYPE: DNA
<213> ORGANISM: Artificial Sequence
<220> FEATURE:
```

<223> OTHER INFORMATION: Primer designed for point mutation
<220> FEATURE:
<221> NAME/KEY: misc_feature
<222> LOCATION: (1)..(30)
<223> OTHER INFORMATION: Reverse primer for F436A mutation

<400> SEQUENCE: 72
gcggcagatt ggtggccggg ccgttagggc                                           30

<210> SEQ ID NO 73
<211> LENGTH: 25
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(25)
<223> OTHER INFORMATION: Forward primer for T437S mutation

<400> SEQUENCE: 73
acggcccgtt cagcaatctg ccgcc                                                25

<210> SEQ ID NO 74
<211> LENGTH: 25
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(25)
<223> OTHER INFORMATION: Reverse primer for T437S mutation

<400> SEQUENCE: 74
ggcggcagat tgctgaacgg gccgt                                                25

<210> SEQ ID NO 75
<211> LENGTH: 37
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(37)
<223> OTHER INFORMATION: Forward primer for T437Y mutation

<400> SEQUENCE: 75
gccctaacgg cccgttctat aatctgccgc cgagtat                                   37

<210> SEQ ID NO 76
<211> LENGTH: 37
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(37)
<223> OTHER INFORMATION: Reverse primer for T437Y mutation

<400> SEQUENCE: 76
atactcggcg gcagattata gaacgggccg ttagggc                                   37

<210> SEQ ID NO 77
<211> LENGTH: 28
<212> TYPE: DNA
<213> ORGANISM: Artificial Sequence

```
<220> FEATURE:
<223> OTHER INFORMATION: Primer designed for point mutation
<220> FEATURE:
<221> NAME/KEY: misc_feature
<222> LOCATION: (1)..(28)
<223> OTHER INFORMATION: Forward primer for L439G mutation

<400> SEQUENCE: 77
acggcccgtt caccaatggg ccgccgag                                        28

<210> SEQ ID NO 78
<211> LENGTH: 28
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(28)
<223> OTHER INFORMATION: Reverse primer for L439G mutation

<400> SEQUENCE: 78
ctcggcggcc cattggtgaa cgggccgt                                        28

<210> SEQ ID NO 79
<211> LENGTH: 28
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(28)
<223> OTHER INFORMATION: Forward primer for L439A mutation

<400> SEQUENCE: 79
acggcccgtt caccaatgcg ccgccgag                                        28

<210> SEQ ID NO 80
<211> LENGTH: 28
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(28)
<223> OTHER INFORMATION: Reverse primer for L439A mutation

<400> SEQUENCE: 80
ctcggcggcg cattggtgaa cgggccgt                                        28

<210> SEQ ID NO 81
<211> LENGTH: 27
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(27)
<223> OTHER INFORMATION: Forward primer for M457L mutation

<400> SEQUENCE: 81
tctggtggca cacttgcgtc agcacgg                                         27

<210> SEQ ID NO 82
<211> LENGTH: 27
<212> TYPE: DNA
```

```
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(27)
<223> OTHER INFORMATION: Reverse primer for M457L mutation

<400> SEQUENCE: 82
ccgtgctgac gcaagtgtgc caccaga                                       27

<210> SEQ ID NO 83
<211> LENGTH: 33
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(33)
<223> OTHER INFORMATION: Forward primer for I495F mutation

<400> SEQUENCE: 83
ccaggtggaa agctggttct ttggcgcaaa cag                                33

<210> SEQ ID NO 84
<211> LENGTH: 33
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(33)
<223> OTHER INFORMATION: Reverse primer for I495F mutation

<400> SEQUENCE: 84
ctgtttgcgc caaagaacca gctttccacc tgg                                33

<210> SEQ ID NO 85
<211> LENGTH: 33
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(33)
<223> OTHER INFORMATION: Forward primer for I495V mutation

<400> SEQUENCE: 85
ccaggtggaa agctgggtct ttggcgcaaa cag                                33

<210> SEQ ID NO 86
<211> LENGTH: 33
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(33)
<223> OTHER INFORMATION: Reverse primer for I495V mutation

<400> SEQUENCE: 86
ctgtttgcgc caaagaccca gctttccacc tgg                                33

<210> SEQ ID NO 87
<211> LENGTH: 35
```

```
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(35)
<223> OTHER INFORMATION: Forward primer for M508L mutation

<400> SEQUENCE: 87
gtaagaagca taccctgttg ttttatctgg ccggc                          35

<210> SEQ ID NO 88
<211> LENGTH: 35
<212> TYPE: DNA
<213> ORGANISM: Artificial Sequence
<220> FEATURE:
<223> OTHER INFORMATION: Primer designed for point mutation
<220> FEATURE:
<221> NAME/KEY: misc_feature
<222> LOCATION: (1)..(35)
<223> OTHER INFORMATION: Reverse primer for M508L mutation

<400> SEQUENCE: 88
gccggccaga taaaacaaca gggtatgctt cttac                          35
```

MONOOXYGENASE MUTANT, PREPARATION METHOD AND APPLICATION THEREOF

INCORPORATION BY REFERENCE

In compliance with 37 C.F.R.§ 1.52(e)(5), M. P. E. P. § 608.05(I), the sequence information contained in electronic file name {SEQ_List_Final.txt}; created on Jul. 27, 2020 using Patent In 3.5.1, is 32,908 bytes in size and is hereby incorporated by reference in its entirety.

TECHNICAL FIELD

The invention relates to the technical field of genetic engineering, in particular to a monooxygenase mutant and a preparation method and application thereof.

BACKGROUND

The chiral sulfoxide widely exists in nature, is a structural unit of many important bioactive molecules, and is an important intermediate for the synthesis of natural products and chiral drugs. Many chiral sulfoxides contain one or more chiral centers, and there are significant differences in pharmacological activity, metabolic processes, metabolic rates, and toxicity of different chiral drugs, typically one enantiomer is effective, while the other enantiomer is inefficient or ineffective, or even toxic. Therefore, how to construct compounds containing chiral centers with high stereoselectivity is of great significance in pharmaceutical research and development.

Baeyer Villiger monooxygenases (BVMOs), belonging to the flavin monooxygenase, are commonly used to stereoselectively oxidize chain and cyclic ketones to form corresponding esters or lactones, and can also catalyze the electrophilic oxidation of sulfur, nitrogen and phosphorus, meanwhile BVMOs can also catalyze the nucleophilic oxidation of ketone and boron. Cyclohexanone monooxygenases (CHMOs) are the first discovered member of BVMO family. CN 105695425A discloses that CHMOs have great application in the synthesis of chiral drugs, can catalyze the oxidation of sulfur-containing chiral precursors, and can be used in the synthesis of chiral drugs modafinil and omeprazole, but the existing CHMOs have low enzyme activity, poor stability, poor soluble expression, low selectivity, large enzyme addition amount and difficult post-treatment.

CHMO, a monooxygenase derived from the monad *Brachymonas petroleovorans*, can catalyze the conversion of sulfide with high selectivity, but it has low activity, poor stability, poor soluble expression in *Escherichia coli* (*E. coli*), and more amount of enzyme are added during the reaction.

CN 107384880A discloses a flavin monooxygenase mutant and a preparation method thereof, wherein error-prone PCR technology is used for carrying out random mutation on wild-type flavin monooxygenase to obtain the flavin monooxygenase mutant, and the specific enzyme activity of the flavin monooxygenase mutant is increased by 35% compared with that of the wild-type flavin monooxygenase. However, it merely improves the specific enzyme activity, and does not contribute to the stability, soluble expression, selectivity of monooxygenase and the amount of enzyme used.

Although several kinds of CHMOs have been used commercially, there are some problems in CHMOs, such as poor soluble expression, low enzyme activity, low enzyme stability and low selectivity. In general, the wild enzyme can be modified by means of directed evolution to improve various properties of the enzyme, so that the wild enzyme can be applied to production.

SUMMARY

Aiming at the defects of the prior art and the actual needs, the invention provides a monooxygenase mutant and a preparation method and application thereof, wherein the monooxygenase mutant improves the transformation efficiency and the stability and is beneficial to the application of the monooxygenase mutant in the pharmaceutical field.

In order to achieve the purpose, the present invention adopts the following technical solutions:

In the first aspect, the present invention provides a monooxygenase mutant having any one of the amino acid sequences shown in (I) and (II):

(I) an amino acid sequence having at least 80% identity to the amino acid sequence shown in SEQ ID NO. 1;

(II) an amino acid sequence obtained by modifying, substituting, deleting, or adding one or several amino acids to the amino acids at 23 to 508 positions of the amino acid sequence shown in SEQ ID NO. 1;

the substituting referring to a substitution of 1 to 34 amino acids;

and wherein the mutant has monooxygenase activity.

In the present invention, the inventors examined the properties of monooxygenases by designing mutations at a plurality of different sites of amino acids 23 to 508, and found that the mutations at these sites can improve the activity, stability, soluble expression and selectivity of monooxygenases, and also can reduce the amount of enzyme used.

According to the invention, the amino acid sequence shown in SEQ ID NO. 1 is as follows:

MSSSPSSAIHFDAIVVGAGFGGMYMLHKLRDQLGLKVKVFDTAGGIGGTW
YWNRYPGALSDTHSHVYQYSFDEAMLQEWTWKNKYLTQPEILAYLEYVAD
RLDLRPDIQLNTTVTSMHFNEVHNIWEVRTDRGGYYTARFIVTALGELSA
INWPNIPGRESFQGEMYHTAAWPKDVELRGKRVGVIGTGSTGVQLITAIA
PEVKHLTVFQRTPQYSVPTGNRPVSAQEIAEVKRNFSKVWQQVRESAVAF
GFEESTVPAMSVSEAERQRVFQEAWNQGNGFYYMEGTFCDIATDPQANEA
AATFIRNKIAEIVKDPETARKLTPTDVYARRPLCDSGYYRTYNRSNVSLV
DVKATPISAMTPRGIRTADGVEHELDMLILATGYDAVDGNYRRIDLRGRG
GQTINEHWNDTPTSYVGVSTANFPNMFMILGPNGPFTNLPPSIEAQVEWI
TDLVAHMRQHGLATAEPTRDAEDAWGRTCAEIAEQTLFGQVESWIFGANS
PGKKHTLMFYLAGEGNYRKQLADVANAQYQGFAFQPL,

In other embodiments of the invention, the amino acid sequence of the monooxygenase mutant has a sequence at least 80% identity to the amino acid sequence of the monooxygenase and has monooxygenase activity.

In some embodiments of the invention, the amino acid sequence of the monooxygenase mutant has a sequence at least 85% identity to the amino acid sequence of the monooxygenase and has monooxygenase activity.

In some embodiments of the invention, the amino acid sequence of the monooxygenase mutant has a sequence at least 90% identity to the amino acid sequence of the monooxygenase and has monooxygenase activity.

In some embodiments of the invention, the amino acid sequence of the monooxygenase mutant has a sequence at least 95% identity to the amino acid sequence of the monooxygenase and has monooxygenase activity.

In the present invention, the modification includes any one or a combination of at least two of amidation, phosphorylation, methylation, acetylation, ubiquitination, glycosylation or carbonylation.

The substitution may be, for example, substitution of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34.

In the present invention, the monooxygenase mutant can catalyze the conversion of sulfide compound, the sulfide compound is

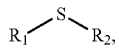

wherein R1 and R2 are each independently a C1-C8 alkyl, a C5-C10 cycloalkyl, a C5-C10 aryl, or a C5-C10 heteroaryl, or R1 and R2 together with the carbon on the carbonyl form a C5-C10 heterocyclyl, a C5-C10 carbocyclyl or a C5-C10 heteroaryl, the heteroatoms in the C5-C10 heterocyclyl and C5-C10 heteroaryl are each independently selected from at least one of nitrogen, oxygen and sulfur, the aryl in the C5-C10 aryl, the heteroaryl in the C5-C10 heteroaryl, the carbocyclyl in the C5-C10 carbocyclyl, or the heterocyclyl in the C5-C10 heterocyclyl is each independently unsubstituted or substituted with at least one of halogen, alkoxy and alkyl, preferably, the sulfide compound is shown in formula I;

The specific reaction formula is as follows:

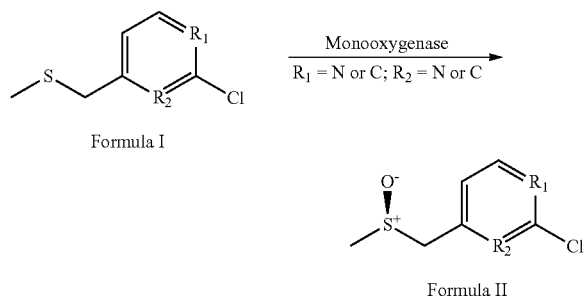

According to the invention, the substitution is the substitution of any one or at least two amino acids at position 23, 25, 47, 75, 93, 106, 110, 117, 137, 153, 159, 166, 260, 265, 284, 289, 334, 359, 360, 377, 380, 426, 428, 435, 436, 437, 439, 457, 474, 479, 490, 495, 500 or 508.

According to the invention, the mutation site of the mutant is any one or combinations of at least two of M23L, M25A, A74D, M75L, A93E, P106R, L110F, M117A, T137R, W153F, R159L, M166L, M260L, A265E, M284I, C289S, C334L, A359E, M360I, M377V, L380F, M426L, M428F, P435L, P435A, F436L, F436Y, F436A, T437S, T437A, T437Y, L439G, L439A, L439S, M457L, A474E, C479V, Q490K, I495F, I495V, I495A, S500I or M508L.

In the present invention, through further experimental verification, the inventors found that the mutation at the 43 positions can further improve the properties of the monooxygenase, wherein mutations at positions 25, 106, 159, 265, 289, 377, 380, 435, 436, 437, 439, 474, 479, 490, 495 or 500 significantly increase the catalytic activity, transformation rate and isopropanol tolerance of monooxygenases. Mutations at other sites can significantly increase the soluble expression and selectivity of the monooxygenase.

According to the invention, the substitution is the substitution of any one or at least two amino acids at positions 25, 106, 159, 265, 289, 377, 380, 435, 436, 437, 439, 474, 479, 490, 495 or 500.

According to the invention, the mutation site of the mutant is any one or a combination of at least two of M25A, P106R, R159L, A265E, C289S, M377V, L380F, P435L, F436Y, T437A, L439S, A474E, C479V, Q490K, I495A or S500I.

According to the invention, when the mutation site of the mutant is any one or a combination of at least two of M25A, P106R, R159L, A265E, C289S, M377V, L380F, P435L, F436Y, T437A, L439S, A474E, C479V, Q490K, I495A or S500I, the transformation rate of the mutant monooxygenase is 40% or more.

According to the invention, the substitution is the substitution of any one or at least two amino acids at position 25, 106, 265, 474, 490 or 500.

According to the invention, the mutation site of the mutant is any one or a combination of at least two of M25A, P106R, A265E, A474E, Q490K or S500I.

According to the invention, when the mutation site of the mutant is any one or a combination of at least two of M25A, P106R, A265E, A474E, Q490K or S500I, the transformation rate of the mutant monooxygenase is 48% or more.

According to the invention, through further investigation, the inventors found that the yield of the five mutants of S500I-A265E-M25A, S500I-A265E-M25A-Q490K, S500I-A265E-M25A-A474E-P106R, S500I-A265E-M25A-Q490K-P106R and S500I-A265E-M25A-A474E-Q490K is the highest and can reach more than 86%, the residual activity of the enzyme in isopropanol can reach more than 60%, and the transformation rate can reach more than 90%.

In the second aspect, the present invention provides a nucleotide sequence encoding a monooxygenase mutant according to the first aspect.

In the third aspect, the invention provides an expression vector comprising at least one copy of a nucleotide sequence according to the second aspect.

In the fourth aspect, the present invention provides a host cell comprising the expression vector of the third aspect.

In the fifth aspect, the present invention provides a method for preparing a mutant according to the first aspect, comprising:

(1) preparing a recombinant host cell, wherein the recombinant host cell comprises a DNA molecule comprising a nucleic acid sequence encoding the mutant according to the first aspect;

(2) incubating the recombinant host cell in a medium suitable for expressing the mutant;

(3) recovering a polypeptide of the mutant expressed by the host cell in step (2) from the culture medium.

In the sixth aspect, the invention provides a composition comprising a polypeptide of the mutant according to the first aspect.

According to the present invention, the composition is any one or a combination of at least two of dry powder, tablet or liquid.

In the seventh aspect, the invention provides the application of a mutant according to the first aspect in the preparation of a chiral drug.

Compared with the prior art, the invention has the following beneficial effects:

(1) in the invention, by designing mutations at a plurality of different sites of 23 to 508 amino acids, it is found that these mutants improve the activity, stability, soluble expression and selectivity of monooxygenase, and can also reduce the usage of monooxygenase;

(2) Through verification, it is found that on the basis of the original monooxygenase, the individual mutations of the 12 sites, namely, M25A, P106R, R159L, A265E, C289S, M377V, L380F, A474E, C479V, Q490K, I495A and S500I, can improve the activity of monooxygenase, and by combining the mutations of the 12 sites, the yield of the five mutants, S500I-A265E-M25A mutant, S500I-A265E-M25A-Q490K mutant, S500I-A265E-M25A-A474E-P106R mutant, S500I-A265E-M25A-Q490K-P106R mutant and S500I-A265E-M25A-A474E-Q490K mutant is the highest, which can reach more than 86%, the residual activity of enzyme in isopropanol can reach more than 60%, and the transformation rate can reach more than 90%.

DETAILED DESCRIPTION OF THE EMBODIMENTS

In order to further illustrate the technical means adopted by the present invention and the effects thereof, the following detailed description is given to further illustrate the technical solution of the present invention, but the present invention is not limited to the embodiments.

The present invention uses conventional techniques and methods used in the fields of genetic engineering and molecular biology, and general references provide definitions and methods known to those skilled in the art. However, those skilled in the art can adopt other conventional methods, experimental protocol and reagents in the art on the basis of the technical solutions described in the present invention, and are not limited to the specific embodiments of the present invention.

The particular techniques or conditions not specified in the embodiments are in accordance with the techniques or conditions described in the literature in the art, or in accordance with the product specifications. Reagents or instruments used without specifying the manufacturer, are conventional products commercially available through regulatory sources.

Example 1 Monooxygenase Mutant with Single Point Mutation (M25A)

Constructing a Monooxygenase Mutant Gene:

In order to improve the activity, stability, soluble expression and selectivity of monooxygenase CHMO from *Brachymonas petroleovorans* (the amino acid sequence is SEQ ID NO.1, and the nucleotide sequence is SEQ ID NO.2), and reduce the amount of enzyme used, the M25A site was mutated respectively, specific steps are as follows:

The nucleotide sequence shown in SEQ ID NO. 2 is as follows:

ATGAGTAGCAGCCCGAGCAGCGCCATCCACTTTGACGCCATTGTGGTGGG

TGCCGGTTTTGGCGGCATGTATATGCTGCACAAGCTGCGCGACCAGCTGG

GCCTGAAAGTTAAAGTGTTCGACACCGCCGGTGGTATTGGTGGTACCTGG

TACTGGAACCGCTATCCGGGTGCCCTGAGCGACACCCATAGCCACGTGTA

-continued

CCAGTACAGCTTCGATGAGGCCATGCTGCAGGAGTGGACATGGAAAAATA

AATATCTGACCCAGCCGGAAATCCTGGCATATCTGGAATACGTGGCCGAT

CGTCTGGATTTACGCCCTGACATTCAGCTGAACACCACCGTTACCAGCAT

GCATTTTAACGAGGTGCACAATATCTGGGAAGTTCGCACCGATCGTGGCG

GCTACTATACAGCACGCTTCATTGTGACCGCACTGGGTCTGTTAAGTGCC

ATCAACTGGCCGAACATCCCGGGCCGTGAGTCTTTTCAAGGCGAAATGTA

TCATACCGCCGCCTGGCCGAAAGATGTTGAACTGCGCGGCAAGCGCGTGG

GTGTGATCGGTACAGGTAGCACCGGTGTGCAGCTGATCACCGCCATTGCA

CCGGAGGTGAAGCACCTGACCGTTTTTCAGCGTACCCCGCAGTATAGCGT

TCCGACAGGCAATCGCCCGGTTAGCGCCCAGGAAATCGCAGAAGTGAAAC

GCAACTTTAGCAAAGTGTGGCAGCAGGTGCGTGAGAGTGCCGTTGCCTTT

GGCTTTGAGGAAAGCACCGTGCCGGCAATGAGCGTTAGCGAGGCAGAACG

CCAGCGTGTTTTCCAGGAAGCATGGAATCAGGGCAACGGCTTTTACTATA

TGTTTGGCACCTTTTGCGATATCGCCACAGATCCGCAGGCCAACGAGGCA

GCCGCCACCTTCATTCGTAATAAGATCGCCGAAATCGTTAAAGATCCGGA

GACAGCCCGCAAACTGACACCGACAGACGTTTATGCCCGTCGTCCGCTGT

GCGATAGCGGCTACTATCGCACCTACAATCGTAGCAACGTGAGCCTGGTG

GATGTGAAGGCCACCCCGATCAGTGCAATGACCCCGCGCGGCATTCGTAC

CGCAGATGGCGTGGAGCATGAACTGGACATGCTGATTCTGGCAACCGGCT

ACGACGCCGTTGATGCAACTATCGCCGTATTGATCTGCGTGGCCGCGGT

GGCCAGACCATTAACGAACACTGGAATGACACCCCTACCAGCTATGTTGG

CGTGAGCACCGCCAATTTTCCGAACATGTTCATGATTCTGGGCCCTAACG

GCCCGTTCACCAATCTGCCGCCGAGTATCGAAGCCCAGGTGGAATGGATT

ACCGATCTGGTGGCACACATGCGTCAGCACGGTCTGGCAACCGCCGAACC

TACCCGCGATGCCGAAGATGCCTGGGGTCGTACCTGTGCAGAGATTGCCG

AGCAGACCCTGTTCGGCCAGGTGGAAAGCTGGATCTTTGGCGCAAACAGC

CCGGGTAAGAAGCATACCCTGATGTTTTATCTGGCCGGCCTGGGCAATTA

CCGCAAACAGCTGGCCGATGTGGCAAATGCCCAGTATCAGGGCTTTGCCT

TCCAGCCTCTGTAA;

(1) Introducing mutations: designing a primer according to the nucleotide shown in SEQ ID NO. 2, and designing a forward primer and a reverse primer containing the M25A site, wherein the forward primer and the reverse primer are as follows:

```
The forward primer
(SEQ ID NO. 3):
gccggttttggcggcatgtatgcgctgcacaagc.

The reverse primer
(SEQ ID NO. 4):
gcttgtgcagcgcatacatgccgccaaaaccggc.
```

Mixing the primers and a template plasmid, adding high fidelity Taq polymerase KOD-Plus, carrying out full plasmid PCR amplification, and carrying out electrophoresis detection on a PCR product after the PCR is finished, wherein the PCR amplification system is as follows:

| System | Addition amount (μL) | Final concentration |
|---|---|---|
| KOD-Plus enzyme (1.0 U/μL) | 1 | 1.0 U/50 μL |
| 10× PCR buffer solution | 5 | 1× |
| 2 mM dNTP | 5 | 0.2 mM |
| 25 mM MgSO4 | 2 | 1.0 mM |
| forward and reverse primers (10 pmol/μL) | 3 | 0.3 μM |
| DNA Template | 1 | 0.3 μM |
| ddH$_2$O | Adding to 50 μL; | |

Amplification conditions of the PCR reaction are as follows:

| | Reaction Procedure | Number of cycles |
|---|---|---|
| Amplification procedure | 94° C. 2 min | 1 |
| | 98° C 10 s | 20 |
| | 68° C. 4 min | |
| | 4° C. | —; |

(2) transformation: adding Dpn I enzyme, digesting a template, transferring into *E. coli* competent BL21 (DE3), culturing overnight at 37° C., and picking out a monoclone to a test tube;
(3) inducing expression: inoculating from a test tube into a 1.5 L shake flask, culturing at 37° C. until the OD$_{600}$ reduces to 1, reducing the culture temperature to 25° C., and adding IPTG with the final concentration of 0.1 mM to induce expression for 16 h; and
(4) reaction verification: adding substrate (3-chlorobenzyl) dimethyl sulfide 40 mg to 10 mL reaction bottle, add 0.1 M Tris-HCl 9.0, 20 mg isopropanol, 0.4 mg NADP$^+$, 4 mg alcohol dehydrogenase, adding 4 mg monooxygenase CHMO (0.1 wt), mixing well, the total volume is 1 mL, at 50° C., in a shaker at 200 rpm, reacting for 16 hours.

Example 2 Monooxygenase Mutant with Single Point Mutation (P106R)

The P106R is subjected to site-directed mutation, and the specific steps are as follows:
Introducing mutations: designing a forward primer and a reverse primer containing the P106R site, wherein the forward primer and the reverse primer are as follows:

The forward primer
    (SEQ ID NO. 5):
    cgtctggatttacgccgtgacattcagctgaac.

The reverse primer
    (SEQ ID NO. 6):
    gttcagctgaatgtcacggcgtaaatccagacg.

Other methods and steps are the same as example 1.

Example 3 Monooxygenase Mutant with Single Point Mutation (R159L)

Introducing mutations: designing a forward primer and a reverse primer containing the R159L site, wherein the forward primer and the reverse primer are as follows:

The forward primer (SEQ ID NO. 7):
    cgaacatcccgggccttgagtcttttcaagg.

The reverse primer (SEQ ID NO. 8):
    ccttgaaaagactcaaggcccgggatgttcg.

Other methods and steps are the same as example 1.

Example 4 Monooxygenase Mutant with Single Point Mutation (A265E)

Introducing mutations: designing a forward primer and a reverse primer containing the A265E site, wherein the forward primer and the reverse primer are as follows:

The forward primer (SEQ ID NO. 9):
    gagcgttagcgaggaagaacgccagcgtg.

The reverse primer (SEQ ID NO. 10):
    cacgctggcgttcttcctcgctaacgctc.

Other methods and steps are the same as example 1.

Example 5 Monooxygenase Mutant with Single Point Mutation (C289S)

Introducing mutations: designing a forward primer and a reverse primer containing the C289S site, wherein the forward primer and the reverse primer are as follows:

The forward primer (SEQ ID NO. 11):
    tttactatatgtttggcacctttagcgatatcgccacag.

The reverse primer (SEQ ID NO. 12):
    ctgtggcgatatcgctaaaggtgccaaacatatagtaaa.

Other methods and steps are the same as example 1.

Example 6 Monooxygenase Mutant with Single Point Mutation (M377V)

Introducing mutations: designing a forward primer and a reverse primer containing the M377V site, wherein the forward primer and the reverse primer are as follows:

The forward primer (SEQ ID NO. 13):
    ggagcatgaactggacgtgctgattctggcaac.

The reverse primer (SEQ ID NO. 14):
    gttgccagaatcagcacgtccagttcatgctcc.

Other methods and steps are the same as example 1.

Example 7 Monooxygenase Mutant with Single Point Mutation (L380F)

Introducing mutations: designing a forward primer and a reverse primer containing the L380F site, wherein the forward primer and the reverse primer are as follows:

The forward primer (SEQ ID NO. 15):
    agcatgaactggacatgctgattttcgcaaccggctac.

The reverse primer (SEQ ID NO. 16):
    gtagccggttgcgaaaatcagcatgtccagttcatgct.

Example 8 Monooxygenase Mutant with Single Point Mutation (P435L)

Introducing mutations: designing a forward primer and a reverse primer containing the P435L site, wherein the forward primer and the reverse primer are as follows:

```
The forward primer (SEQ ID NO. 17):
gggccctaacggcctgttcaccaatctgc.

The reverse primer (SEQ ID NO. 18):
gcagattggtgaacaggccgttagggccc.
```

Other methods and steps are the same as example 1.

Example 9 Monooxygenase Mutant with Single Point Mutation (F436Y)

Introducing mutations: designing a forward primer and a reverse primer containing the F436Y site, wherein the forward primer and the reverse primer are as follows:

```
The forward primer (SEQ ID NO. 19):
gggccctaacggcccgtataccaatctgccg.

The reverse primer (SEQ ID NO. 20):
cggcagattggtatacgggccgttagggccc.
```

Other methods and steps are the same as example 1.

Example 10 Monooxygenase Mutant with Single Point Mutation (T437A)

Introducing mutations: designing a forward primer and a reverse primer containing the T437A site, wherein the forward primer and the reverse primer are as follows:

```
The forward primer (SEQ ID NO. 21):
taacggcccgttcgccaatctgccgcc.

The reverse primer (SEQ ID NO. 22):
ggcggcagattggcgaacgggccgtta.
```

Other methods and steps are the same as example 1.

Example 11 Monooxygenase Mutant with Single Point Mutation (L439S)

Introducing mutations: designing a forward primer and a reverse primer containing the L439S site, wherein the forward primer and the reverse primer are as follows:

```
The forward primer (SEQ ID NO. 23):
cctaacggcccgttcaccaattcgccgccgagta.

The reverse primer (SEQ ID NO. 24):
tactcggcggcgaattggtgaacgggccgttagg.
```

Other methods and steps are the same as example 1.

Example 12 Monooxygenase Mutant with Single Point Mutation (A474E)

Introducing mutations: designing a forward primer and a reverse primer containing the A474E site, wherein the forward primer and the reverse primer are as follows:

```
The forward primer (SEQ ID NO. 25):
gcgatgccgaagatgagtggggtcgtacctg.

The reverse primer (SEQ ID NO. 26):
caggtacgacccactcatcttcggcatcgc.
```

Other methods and steps are the same as example 1.

Example 13 Monooxygenase Mutant with Single Point Mutation (C479V)

Introducing mutations: designing a forward primer and a reverse primer containing the C479V site, wherein the forward primer and the reverse primer are as follows:

```
The forward primer (SEQ ID NO. 27):
gcctggggtcgtaccgttgcagagattgccga.

The reverse primer (SEQ ID NO. 28):
tcggcaatctctgcaacggtacgacccaggc.
```

Other methods and steps are the same as example 1.

Example 14 Monooxygenase Mutant with Single Point Mutation (Q490K)

Introducing mutations: designing a forward primer and a reverse primer containing the Q490K site, wherein the forward primer and the reverse primer are as follows:

```
The forward primer (SEQ ID NO. 29):
agaccctgttcggcaaggtggaaagctgg.

The reverse primer (SEQ ID NO. 30):
ccagatttccaccttgccgaacagggtct.
```

Other methods and steps are the same as example 1.

Example 15 Monooxygenase Mutant with Single Point Mutation (I495A)

Introducing mutations: designing a forward primer and a reverse primer containing the I495A site, wherein the forward primer and the reverse primer are as follows:

```
The forward primer (SEQ ID NO. 31):
ccaggtggaaagctgggcctttggcgcaaacagc.

The reverse primer (SEQ ID NO. 32):
gctgtttgcgccaaaggcccagctttccacctgg.
```

Other methods and steps are the same as example 1.

Example 16 Monooxygenase Mutant with Single Point Mutation (S500I)

Introducing mutations: designing a forward primer and a reverse primer containing the S500I site, wherein the forward primer and the reverse primer are as follows:

```
The forward primer (SEQ ID NO. 33):
gctggatctttggcgcaaacatcccgggtaaga.

The reverse primer (SEQ ID NO. 34):
tcttacccgggatgtttgcgccaaagatccagc.
```

Other methods and steps are the same as example 1.

Transformation Rate Detection

Adding 3 mL acetonitrile into a reaction sample system, uniformly mixing, placing into a 5 mL EP tube, centrifuging at 12000 rpm for 3 minutes, taking 100 μL supernatant into a sample feeding bottle, adding 900 μL 90% acetonitrile, detecting by HPLC with detection wavelength of 210 nm, the results are shown in table 1.

Stability Detection

Taking two parts of monooxygenase SEQ ID NO: 1 with a mass of 4 mg, adding isopropanol with a final concentration of 10% in one part and standing for 1 h at 30° C. and the other part was isopropanol-free and standing for 1 h at 30° C., and the reaction was carried out according to the following system:

adding substrate (3-chlorobenzyl) dimethyl sulfide 40 mg to 10 mL reaction bottle, add 0.1 M Tris-HCl 9.0, 20 mg isopropanol, 0.4 mg NADP$^+$, 4 mg alcohol dehydrogenase, adding 4 mg monooxygenase CHMO, mixing well, the total volume is 1 mL, at 50° C., in a shaker at 200 rpm, reacting for 16 hours. Adding 3 mL acetonitrile into a reaction sample system, uniformly mixing, placing into a 5 mL EP tube, centrifuging at 12000 rpm for 3 minutes. Taking 100 μL supernatant into a sample feeding bottle, adding 900 μL 90% acetonitrile, detecting by HPLC with detection wavelength of 210 nm.

Mutant stability is expressed as the percentage of monooxygenase transformation rate incubated in isopropanol versus monooxygenase transformation rate incubated without isopropanol, and the results are shown in Table 1.

TABLE 1

| Mutant | Mutation site | Amount of enzyme used | Transformation rate (%) | Residual viability (%) |
|---|---|---|---|---|
| Control | N/A | 0.2 wt | 35.1 | 50.3 |
| Example 1 | M25A | 0.1 wt | 48.1 | 47.2 |
| Example 2 | P106R | 0.1 wt | 55.5 | 51.1 |
| Example 3 | R159L | 0.1 wt | 67.8 | 43.5 |
| Example 4 | A265E | 0.1 wt | 59.7 | 62.7 |
| Example 5 | C289S | 0.1 wt | 72.5 | 46.8 |
| Example 6 | M377V | 0.1 wt | 53.7 | 57.5 |
| Example 7 | L380F | 0.1 wt | 56.6 | 56.3 |
| Example 8 | P435L | 0.1 wt | 41.2 | 45.7 |
| Example 9 | F436Y | 0.1 wt | 48.5 | 50.6 |
| Example 10 | T437A | 0.1 wt | 44.4 | 49.6 |
| Example 11 | L439S | 0.1 wt | 40.9 | 47.8 |
| Example 12 | A474E | 0.1 wt | 52.5 | 64.8 |
| Example 13 | C479V | 0.1 wt | 57.5 | 46.6 |
| Example 14 | A490K | 0.1 wt | 58.2 | 60.2 |
| Example 15 | I495A | 0.1 wt | 62.1 | 42.1 |
| Example 16 | S500I | 0.1 wt | 60.6 | 59.2 |

As can be seen from Table 1, the transformation effect of the single point mutant was improved compared with that of the parent, but the desired effect was not achieved. The residual activity in isopropanol of Examples 4 (A265E), 8 (A474E) and 10 (A490K) of the single point mutant was improved to more than 60%. In general, the performance of mutants with single point mutation is hardly different from that of the parent, and better mutants can be obtained by the combination of mutation sites.

Example 17 Monooxygenase Mutant with Single Point Mutation

Introducing mutations: designing forward primers and reverse primers containing 23 additional sites (M23L, A74D, M75L, A93E, L110F, M117A, T137R, W153F, M166L, M260L, M284I, C334L, A359E, M360I, M426L, M428F, P435A, F436L, F436A, T437S, T437Y, L439G, L439A, M457L, I495F, I495V or M508L), respectively, with the specific primers listed in the following Table 2:

TABLE 2

| Site | Forward primer | Reverse primer |
|---|---|---|
| M23L (SEQ ID NO. 35-36) | gccggttttggcggcttgtatatgctgcaca | tgtgcagcatatacaagccgccaaaaccggc |
| A74D (SEQ ID NO. 37-38) | acagcttcgatgaggacatgctgcaggagtg | cactcctgcagcatgtcctcatcgaagctgt |
| M75L (SEQ ID NO. 39-40) | gcttcgatgaggccttgctgcaggagtgg | ccactcctgcagcaaggcctcatcgaagc |
| A93E (SEQ ID NO. 41-42) | ccagccggaaatcctggaatatctggaatacgtgg | ccacgtattccagatattccaggatttccggctgg |
| L110F (SEQ ID NO. 43-44) | tacgccctgacattcagttcaacaccaccgttaccag | ctggtaacggtggtgttgaactgaatgtcagggcgta |
| M117A (SEQ ID NO. 45-46) | gaacaccaccgttaccagcgcgcatttaacgaggtgcacgtgcacctcgttaaaatgcgcgctggtaacggtggtgttc | |
| T137R (SEQ ID NO. 47-48) | gatcgtggcggctactatagagcacgcttca | tgaagcgtgctctatagtagccgccacgatc |
| W153F (SEQ ID NO. 49-50) | cgggatgttcgggaagttgatggcacttaacagaccc | gggtctgttaagtgccatcaacttcccgaacatcccg |
| M166L (SEQ ID NO. 51-52) | tgagtcttttcaaggcgaattgtatcataccgccg | cggcggtatgatacaattcgccttgaaaagactca |
| M260L (SEQ ID NO. 53-54) | gcaccgtgccggcattgagcgttagcg | cgctaacgctcaatgccggcacggtgc |

TABLE 2-continued

| Site | Forward primer | Reverse primer |
|---|---|---|
| M284I (SEQ ID NO. 55-56) | atcagggcaacggclllllactatatatttggcaccttttgc | aaaaggtgccaaatatatagtaaaagccgttgccctgat |
| C334L (SEQ ID NO. 57-58) | gcccgtcgtccgctgttagatagcggctactatc | gatagtagccgctatctaacagcggacgacgggc |
| A359E (SEQ ID NO. 59-60) | accccgatcagtgaaatgaccccgcgc | gcgcggggtcatttcactgatcggggt |
| M360I (SEQ ID NO. 61-62) | accccgatcagtgcaataaccccgcgc | gcgcggggttattgcactgatcggggt |
| M426L (SEQ ID NO. 63-64) | ccgccaattttccgaacttgttcatgattctgggc | gcccagaatcatgaacaagttcggaaaattggcgg |
| M428F (SEQ ID NO. 65-66) | caattaccgaacatgttcttcattctgggccctaacggccggccgttagggc | ccagaatgaagaacatgttcggaaaattg |
| P435A (SEQ ID NO. 67-68) | gggccctaacggcgcgttcaccaatct | agattggtgaacgcgccgttagggccc |
| F436L (SEQ ID NO. 69-70) | gccctaacggcccgttaaccaatctgcc | ggcagattggttaacgggccgttagggc |
| F436A (SEQ ID NO. 71-72) | gccctaacggcccggccaccaatctgccgc | gcggcagattggtggccgggccgttagggc |
| T437S (SEQ ID NO. 73-74) | acggcccgttcagcaatctgccgcc | ggcggcagattgctgaacgggccgt |
| T437Y (SEQ ID NO. 75-76) | gccctaacggcccgttctataatctgccgccgagtat | atactcggcggcagattatagaacgggccgttagggc |
| L439G (SEQ ID NO. 77-78) | acggcccgttcaccaatgggccgccgag | ctcgcggcccattggtgaacgggccgt |
| L439A (SEQ ID NO. 79-80) | acggcccgttcaccaatgcgccgccgag | ctcgcggcgcattggtgaacgggccgt |
| M457L (SEQ ID NO. 81-82) | tctggtggcacacttgcgtcagcacgg | ccgtgctgacgcaagtgtgccaccaga |
| I495F (SEQ ID NO. 83-84) | ccaggtggaaagctggttctttggcgcaaacag | ctgtttgcgccaaagaaccagctttccacctgg |
| I495V (SEQ ID NO. 85-86) | ccaggtggaaagctgggtctttggcgcaaacag | ctgtttgcgccaaagacccagctttccacctgg |
| M508L (SEQ ID NO. 87-88) | gtaagaagcatacctgttgattatctggccggc | gccggccagataaaacaacagggtatgcttcttac |

Other methods and steps are the same as example 1.

Verification of Activity

Ultrasonically crushing the cultured strain, and detecting the expression amount of the protein in the supernatant and the precipitate, the results are shown in table 3:

TABLE 3

| Mutation site | Expression of supernatant | Expression of precipitate |
|---|---|---|
| N/A | +++++ | +++++ |
| M23L | +++++ | +++++ |
| A74D | ++++++++ | ++ |
| M75L | +++++ | +++++ |
| A93E | +++++ | +++++ |
| L110F | +++++ | +++++ |
| M117A | +++++ | +++++ |
| T137R | +++++ | +++++ |
| M153F | ++++++ | +++++ |
| M166L | +++++ | +++++ |
| M260L | +++++ | +++++ |
| M284I | +++++ | ++++ |

TABLE 3-continued

| Mutation site | Expression of supernatant | Expression of precipitate |
|---|---|---|
| C334L | +++++ | +++++ |
| A359E | +++++ | +++++ |
| M360I | +++++ | +++++ |
| M426L | +++++ | +++++ |
| M428F | +++++ | +++++++ |
| P435A | +++++ | +++++ |
| F436L | +++++ | +++++ |
| F436A | +++++ | +++++ |
| T437S | +++++ | +++++ |
| T437Y | +++++ | +++++ |
| L439G | +++++ | +++++ |
| L439A | +++++ | +++++ |
| M457L | +++++ | +++++ |
| I495F | +++++ | +++++ |
| I495V | +++++ | +++++ |
| M508L | +++++ | +++++ |

It can be seen from table 3 that although these sites did not increase the transformation rate of monooxygenase, they did increase the soluble expression of monooxygenase, especially A74D and M153F significantly increased the supernatant expression.

Example 18 Monooxygenase Mutant with Multi Point Mutation

Randomly recombining mutation sites through a DNA shuffling method, establishing a mutation library, then screening, and preparing a monooxygenase mutant with multi-point mutation, which comprises the following specific steps of:

(1) obtaining homologous genes with M25A, P106R, A265E, M377V, A474E, C479V, Q490K, I495A and S500I mutation sites by PCR, purifying PCR products, mixing the genes according to equimolar amount, digesting the genes into random fragments by nuclease I, forming a library from the random fragments, and carrying out PCR amplifications with primers and a template mutually; when one gene copy fragment is used as a primer of another gene copy, template exchange and gene recombination occurred, and the reaction system of the N-PCR is as follows:

| System | Addition amount (μL) |
|---|---|
| 10× PFU buffer solution | 5 |
| dNTP | 5 |
| DNA template (80-200 bp) | 6 |
| Pfu polymerase (2.5 U) | 0.5 μL |
| ddH$_2$O | Adding to 50 μL; |

The amplification conditions of the N-PCR reaction are as follows:

| | Reaction Procedure | Number of cycles |
|---|---|---|
| Amplification primer | 95° C. 10 min | 1 |
| | 94° C. 30 s | 5 |
| | 69° C. 30 s | |
| | 72° C. 2 min/1 kb | |
| | 94° C. 30 s | 5 |
| | 69° C. 30 s | |
| | 72° C. 2 min/1 kb | |
| | 94° C. 30 s | 5 |
| | 69° C. 30 s | |
| | 72° C. 2 min/1 kb | |
| | 72° C. 10 min | 1 |
| | 4° C. | —; |

(2) transformation and screening: transferring the prepared product into *E. coli*, and culturing;

(3) preparing enzyme solution: centrifuging a 96-well plate to remove a supernatant culture medium, adding 200 μL enzymolysis solution (lysozyme 2 mg/mL, polymyxin 0.5 mg/mL, pH=7.0) into each well, and carrying out heat preservation and crushing at 37° C. for 3 hours;

(4) high-throughput screening: 250 μL activity assay system: the final concentration of the substrate (3-chlorobenzyl) dimethyl sulfide was 2 mM, the final concentration of NADPH was 0.3 mM, the addition amount of a crushing enzyme solution was 100 pt, the pH value was 9.0, the temperature was 30° C., the mutant obtained by screening is subjected to shake flask culture, and then amplification reaction is carried out;

(5) inducing expression: 25° C., 0.1 mM IPTG inducing overnight;

(6) reaction verification: adding 40 mg substrate into 10 mL reaction bottle, add 0.1 M Tris-HCl 9.0, 20 mg isopropanol, 0.4 mg NADP$^+$, 4 mg alcohol dehydrogenase, adding 4 mg monooxygenase CHMO (0.1 wt), mixing well, the total volume is 1 mL, at 50° C., in a shaker at 200 rpm, reacting for 16 hours.

Transformation Rate Detection

Adding 3 mL acetonitrile into a reaction sample system, uniformly mixing, placing into a 5 mL EP tube, centrifuging at 12000 rpm for 3 minutes, taking 100 μL supernatant into a sample feeding bottle, adding 900 μL 90% acetonitrile, detecting by HPLC with detection wavelength of 210 nm, the results are shown in table 2.

Stability Detection

Taking two parts of monooxygenase SEQ ID NO: 1 with a mass of 4 mg, adding isopropanol with a final concentration of 10% in one part and standing for 1 h at 30° C. and the other part was isopropanol-free and standing for 1 h at 30° C., and the reaction was carried out according to the following system:

adding 40 mg substrate into 10 mL reaction bottle, add 0.1 M Tris-HCl 9.0, 20 mg isopropanol, 0.4 mg NADP$^+$, 4 mg alcohol dehydrogenase, adding 4 mg monooxygenase CHMO, mixing well, the total volume is 1 mL, at 50° C., in a shaker at 200 rpm, reacting for 16 hours. Adding 3 mL acetonitrile into a reaction sample system, uniformly mixing, placing into a 5 mL EP tube, centrifuging at 12000 rpm for 3 minutes. Taking 100 μL supernatant into a sample feeding bottle, adding 900 μL 90% acetonitrile, detecting by HPLC with detection wavelength of 210 nm.

Mutant stability is expressed as the percentage of monooxygenase transformation rate incubated in isopropanol versus monooxygenase transformation rate incubated without isopropanol, and the results are shown in Table 4.

TABLE 4

| Mutatation site | Amount of enzyme used | Transformation (%) | Residual viability (%) |
|---|---|---|---|
| N/A | 0.2 wt | 35.1 | 50.3 |
| M25A-C479V | 0.1 wt | 52.8 | 47.5 |
| M25A-S500I | 0.1 wt | 65.1 | 45.6 |
| S500I-P106R | 0.1 wt | 69.9 | 52.3 |
| S500I-A265E | 0.1 wt | 85.5 | 60.4 |
| S500I-A474E | 0.1 wt | 66.3 | 61.7 |
| S500I-Q490K | 0.1 wt | 75.3 | 58.7 |
| S500I-A265E-M25A | 0.1 wt | 96.3 | 69.5 |
| S500I-A265E-P106R | 0.1 wt | 73.3 | 47.8 |
| S500I-A265E-A474E | 0.1 wt | 84.9 | 58.6 |
| S500I-A265E-Q490K | 0.1 wt | 61.4 | 55.4 |
| M377V-M25A-C289S | 0.1 wt | 23.6 | 50.1 |
| M377V-M25A-C479V | 0.1 wt | 28.8 | 49.3 |
| M377V-M25A-S500I | 0.1 wt | 45.5 | 54.7 |
| S500I-A265E-M25A-P106R | 0.1 wt | 16.9 | 61.5 |
| S500I-A265E-M25A-A474E | 0.1 wt | 97.1 | 59.3 |
| S500I-A265E-M25A-Q490K | 0.1 wt | 97.0 | 55.8 |
| S500I-A265E-M25A-A474E-P106R | 0.1 wt | 97.1 | 67.5 |
| S500I-A265E-M25A-Q490K-P106R | 0.1 wt | 96.5 | 63.2 |
| S500I-A265E-M25A-A474E-Q490K | 0.1 wt | 97.1 | 66.1 |
| S500I-A265E-M25A-A474E-Q490K-I495A | 0.1 wt | 72.2 | 49.5 |
| 5500I-A265E-M25A-I495A | 0.1 wt | 65.0 | 47.6 |
| S500I-A265E-M25A-A474E-I495A | 0.1 wt | 59.0 | 43.9 |

It can be seen from Table 4 that most of the transformation effects of multipoint mutants are further improved compared with single point mutants, and a small part of them have no improvement in transformation effect, but the stability is improved. It can be seen that multipoint mutations will further improve the properties of monooxygenase. Among the multipoint mutants, the transformation rates of S500I-A265E-M25A mutants, S500I-A265E-M25A-A474E mutants, S500I-A265E-M25A-Q490K mutants, S500I-A265E-M25A-A474E-P106R mutants, S500I-A265E-M25A-Q490K-P106R mutants and S500I-A265E-M25A-A474E-Q490K mutants can reach more than 90%, and the residual activity in isopropanol can reach more than 60%. The amplification effect of the six mutants was further verified.

Example 19 Verification of Amplification Reaction of Multi-Point Mutants

Further verify the yield of the prepared S500I-A265E-M25A mutant, S500I-A265E-M25A-A474E mutant, S500I-A265E-M25A-Q490K mutant, S500I-A265E-M25A-A474E-P106R mutant, S500I-A265E-M25A-Q490K-P106R mutant and S500I-A265E-M25A-A474E-Q490K mutant, the specific steps are as follows:

(1) adding substrate (3-chlorobenzyl) dimethyl sulfide 1 g to 250 mL reaction bottle, add 0.1 M Tris-HCl 9.0, 500 mg isopropanol, 10 mg NADP⁺, 100 mg alcohol dehydrogenase, adding 100 mg monooxygenase CHMO, mixing well, the total volume is 25 mL, at 50° C., in a shaker at 200 rpm, reacting for 16;

(2) sampling 1 mL from the reaction sample system, adding 3 ml acetonitrile, uniformly mixing, placing in a 5 ml EP tube, and centrifuging at 12000 rpm for 3 minutes. Taking 100 μL supernatant into a sample feeding bottle, adding 900 μL 90% acetonitrile, detecting by HPLC with detection wavelength of 210 nm;

(3) after the reaction is finished, adding 50 mL ethyl acetate for extraction three times, combining the extracted organic phases, adding magnesium sulfate for drying, performing rotary evaporation to dryness, and weighing, and the results are shown in Table 5:

TABLE 5

| Mutation site | Yield (%) | e.e. (%) |
|---|---|---|
| S500I-A265E-M25A | 86.5 | 99 |
| S500I-A265E-M25A-A474E | 89.5 | 99 |
| S500I-A265E-M25A-Q490K | 90.2 | 99 |
| S500I-A265E-M25A-A474E-P106R | 88.9 | 99 |
| S500I-A265E-M25A-Q490K-P106R | 90.8 | 99 |
| S500I-A265E-M25A-A474E-Q490K | 89.3 | 99 |

As can be seen from Table 5, the yield of the six mutants can reach more than 86%, the e. e. values are all 99%, in particular, the yield of the (5500I-A265E-M25A-Q490K-) mutant can reach 90.2% with e. e. value of 99%, it can be seen that multi-site mutations have achieved good results.

In summary, through verification, it is found that on the basis of the original monooxygenase, the individual mutations of the 12 sites, namely, M25A, P106R, R159L, A265E, C289S, M377V, L380F, A474E, C479V, Q490K, I495A and S500I, can improve the activity of monooxygenase, and by combining the mutations of the 12 sites, the yield of the five mutants, S500I-A265E-M25A mutant, S500I-A265E-M25A-Q490K mutant, S500I-A265E-M25A-A474E-P106R mutant, S500I-A265E-M25A-Q490K-P106R mutant and S500I-A265E-M25A-A474E-Q490K mutant is the highest, which can reach more than 86%, the residual activity of enzyme in isopropanol can reach more than 60%, and the transformation rate can reach more than 90%.

The applicant states that the present invention illustrates a detailed method of the present invention by way of the above-described embodiments, but the present invention is not limited to the above-described detailed method, that is, it does not mean that the present invention must be carried out depending on the above-described detailed method. It should be apparent to those skilled in the art that any modification of the present invention, equivalent substitution of raw materials, addition of auxiliary components, selection of specific modes, and the like, for the products of the present invention all fall within the scope of protection and disclosure of the present invention.

What is claimed is:

1. A monooxygenase mutant with monooxygenase activity, wherein the monooxygenase mutant comprises the amino acid sequence of SEQ ID NO: 1, except for the substitution S500I and optionally one or more additional substitutions selected from the group consisting of M25A, P106R, A265E, M377V, A474E, Q490K, I495A, M23L, A74D, M75L, A93E, L110F, M117A, T137R, W153F, R159L, M166L, M260L, M284I, C289S, C334L, A359E, M360I, L380F, M426L, M428F, P435L, P435A, F436L, F436Y, F436A, T437S, T437A, T437Y, L439G, L439A, L439S, M457L, C479V, I495F, I495V and M508L, wherein the amino acid numbering corresponds to the amino acid sequence of SEQ ID NO: 1.

2. A nucleic acid comprising a nucleotide sequence encoding the monooxygenase mutant according to claim 1.

3. An expression vector comprising the nucleic acid according to claim 2.

4. An isolated host cell comprising the expression vector according to claim 3.

5. A method for preparing the monooxygenase mutant according to claim 1, comprising:
(1) preparing a recombinant host cell, wherein the recombinant host cell comprises a DNA molecule comprising a nucleic acid sequence encoding the monooxygenase mutant according to claim 1;
(2) incubating the recombinant host cell in a culture medium suitable for expressing the monooxygenase mutant; and
(3) recovering of the monooxygenase mutant from the culture medium.

6. A composition comprising the monooxygenase mutant according to claim 1.

7. The monooxygenase mutant according to claim 1, wherein the one or more additional substitutions are selected from the group consisting of M25A, P106R, A265E, M377V, A474E, Q490K, I495A, R159L, C289S, L380F, P435L, F436Y, T437A, L439S, and C479V.

8. The monooxygenase mutant according to claim 1, wherein the one or more additional substitutions are selected from the group consisting of M25A, P106R, A265E, A474E and Q490K.

9. The composition according to claim 6, wherein the composition is a dry powder, a tablet or a liquid.

* * * * *